United States Patent [19]

Meyer

[11] 4,141,368
[45] Feb. 27, 1979

[54] TEMPORARY CERVICAL IMMOBILIZING ORTHOSIS

[75] Inventor: Paul R. Meyer, Chicago, Ill.

[73] Assignee: Northwestern University, Evanston, Ill.

[21] Appl. No.: 799,592

[22] Filed: May 23, 1977

[51] Int. Cl.² .............................................. A61F 5/04
[52] U.S. Cl. .................................... 128/87 B; 128/134
[58] Field of Search ...................... 128/75, 84 R, 84 C, 128/87 R, 87 B, 134, 83, 76; 5/82; 269/328

[56] References Cited

U.S. PATENT DOCUMENTS

| 1,803,556 | 5/1931 | Nugent | 128/87 B |
| 3,336,922 | 8/1967 | Taylor | 128/75 |
| 3,605,736 | 9/1971 | D'Amico et al. | 128/75 |
| 3,724,453 | 4/1973 | Dixon et al. | 128/87 R |
| 3,737,923 | 6/1973 | Prolo | 5/82 |
| 4,034,748 | 7/1977 | Winner | 128/87 R |

OTHER PUBLICATIONS

"Special Centers for the Care of the Injured", by P. R. Meyer et al., 1973, vol. 13, No. 4, The Journal of Trauma, p. 311, FIG. 2.

Primary Examiner—John D. Yasko

[57] ABSTRACT

A device for immobilizing the cranium and cervical spine of a patient comprises an orthosis which is adapted to engage the shoulders and head of the patient and straps for attaching the orthosis to the patient. The orthosis includes a curved shoulder portion for engaging the back of the shoulders of the patient, a V-shaped head portion for engaging the back of the head, and a top portion which extends transversely across the top of the V-shaped head portion. Elastic stabilizing or traction straps extend through the top portion and are secured to the orthosis, and traction or head neck stability can be applied to the patient's head by a halter or skeletal tongs attached to the straps.

9 Claims, 10 Drawing Figures

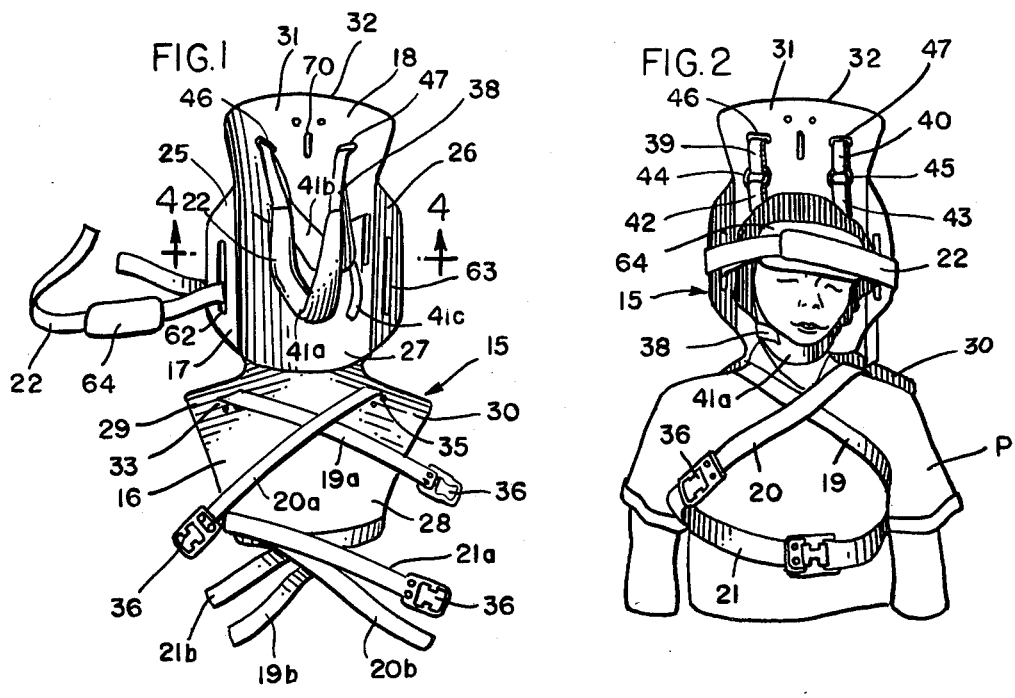
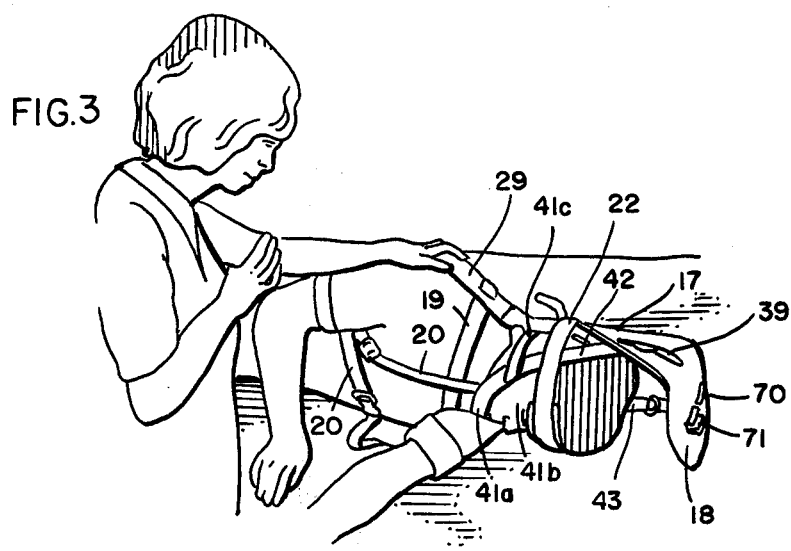
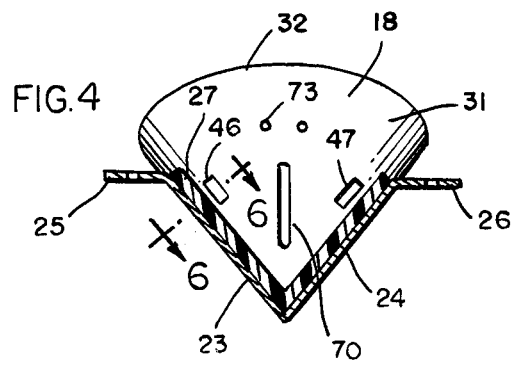

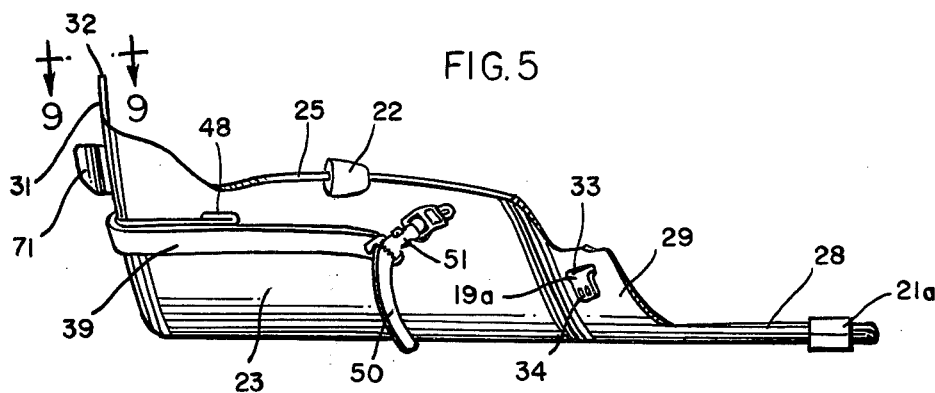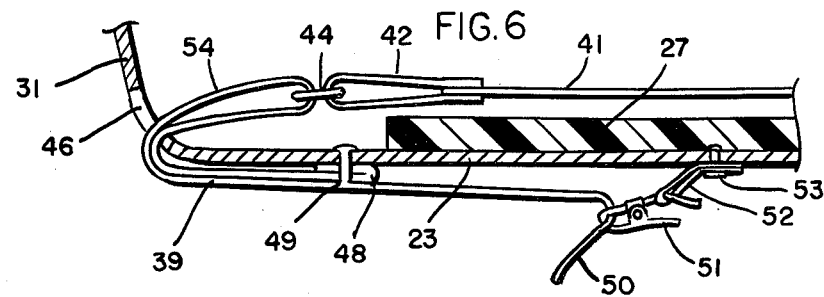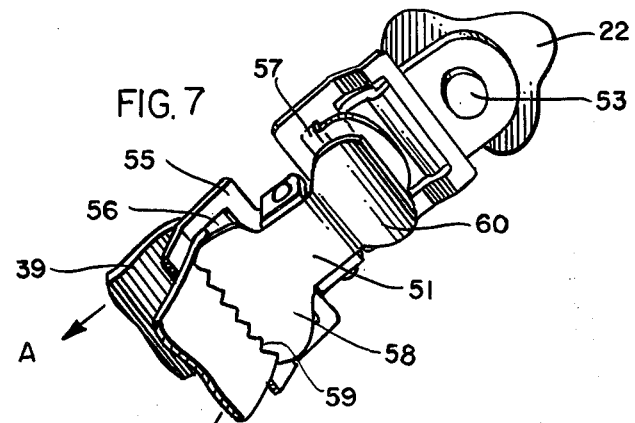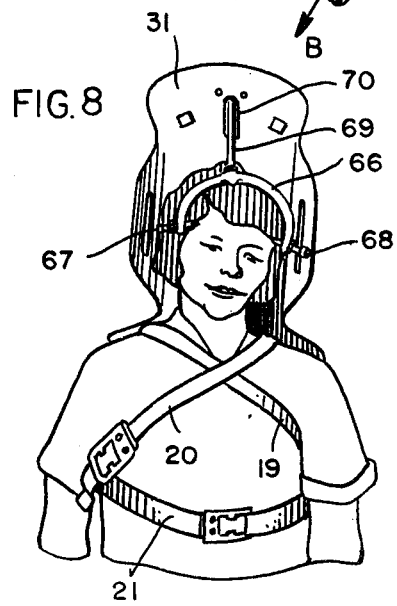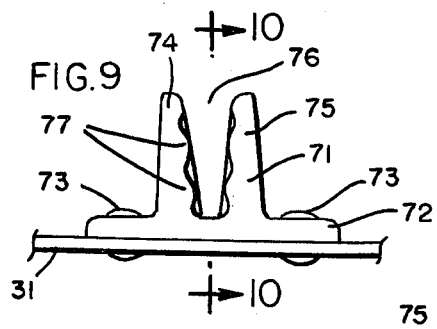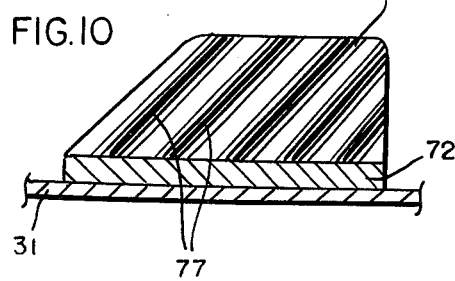

TEMPORARY CERVICAL IMMOBILIZING ORTHOSIS

BACKGROUND AND SUMMARY

This invention relates to a cervical orthosis for use with a patient having a cervical spine injury, and, more particularly, to an orthosis which immobilizes the cranium and cervical spine.

Care of the patient with a spinal injury correctly and necessarily begins at the scene of the accident. It is desirable to stabilize the spine of the patient before transporting the patient to a hospital in order to reduce the risk of any further injury. A splint or orthosis for this purpose should be capable of being easily and correctly applied by ambulance personnel without causing additional injury and should immobilize the cervical area of the spine while the patient is transported. A typical method of immobilizing the cervical spine prior to the invention involved the use of a backboard to which the patient was strapped or taped with adhesive tape, or held between two sand bags. Traction might be applied to the head by the use of skeletal tongs and a weight which was connected to the tongs by a cord.

Prior immobilizing devices have not been entirely satisfactory. For example, it is not unusual for an injured patient to experience emesis, and during emesis a patient must be turned on his side. However, with many immobilizing devices it is not possible to turn a patient quickly and easily while maintaining the immobilized relationship of the head, neck, and thoracic spine. Further, when weights are used to provide traction, the weights can swing or move as the transport vehicle turns, accelerates, or decelerates, and the traction force might not be maintained constant.

The invention provides a cervical immobilizing orthosis which can be easily applied to the patient at the scene of the injury, either before or after the patient is extricated. The orthosis is self-retaining and stabilizes the cranium, cervical spine, and thoracic spine. Traction or stability is applied by a head halter, which is provided with dynamic tension via elastic straps attached to the orthosis. A pulley arrangement of the straps allows the desired force to be applied merely by pulling on the ends of the straps. The device provides constant cervical spinal immobilization and/or traction while at the same time allowing resuscitation of the patient, turning of the patient during emesis, and ease of transport, without fear of changing the head, neck, and thoracic spine relationship. The orthosis can also be used to transport the patient from one hospital to another after skeletal traction tongs have already been applied to the patient. The tongs are attached to the orthosis by a cord or the elastic straps, allowing constant cranial-cervical traction to be provided during transport, irrespective of gravity changes associated with acceleration or deceleration of the transporting vehicle.

DESCRIPTION OF THE DRAWING

The invention will be explained in conjunction with an illustrative embodiment shown in the accompanying drawing, in which FIG. 1 is a front elevational view of a cervical immobilizing orthosis formed in accordance with the invention;

FIG. 2 illustrates the orthosis attached to a patient;

FIG. 3 illustrates the patient rolled to a lateral position during emesis;

FIG. 4 is a sectional view taken along the line 4—4 of FIG. 1;

FIG. 5 is a side elevational view of the orthosis;

FIG. 6 is an enlarged fragmentary sectional view taken along the line 6—6 of FIG. 4;

FIG. 7 is an enlarged fragmentary perspective view of one of the clips for the traction straps;

FIG. 8 illustrates the brace used in conjunction with skeletal traction tongs;

FIG. 9 is a view of the attaching cleat for the tongs taken along the line 9—9 of FIG. 5; and FIG. 10 is a fragmentary sectional view of the cleat taken along the line 10—10 of FIG. 9.

DESCRIPTION OF SPECIFIC EMBODIMENT

Referring first to FIGS. 1-4, the numeral 15 designates generally a cervical immobilizing orthosis or brace which includes a bottom or shoulder portion 16, an intermediate or head portion 17, and a top portion 18. The orthosis is attached to the shoulders and chest of a patient P by crossing elastic straps 19 and 20 and a chest strap 21, and a forehead strap 22 extends over the forehead from one side of the head portion to the other.

The head portion 17 is V-shaped in cross section (FIG. 4) and includes a pair of diverging flat walls 23 and 24. The upper edges of the walls terminate in laterally outwardly extending wing portions 25 and 26, respectively. A layer of cushioning material 27, such as form rubber or the like, is applied to the inside surfaces of the walls to provide a cushioned support for the back of the head.

The shoulder portion 16 includes a substantially flat lower or back portion 28 (see also FIG. 5) which is adapted to engage the back and shoulders of the patient, and right and left upper portions 29 and 30 which are contoured to follow the right and left shoulders of the patient. The right curved portion merges with the flat wall 23, and the left curved portion merges with the flat wall 24.

The top portion 18 comprises a substantially flat wall 31 which extends generally transversely between the V-shaped walls of the head portion (FIGS. 4 and 5). The general plane of the top wall 31 is not quite perpendicular to the longitudinal axis of the V-shaped head portion, and a substantial portion of the lower surface of the wall is therefore visible in the front elevational views of FIGS. 1, 2, and 8. Referring to FIG. 4, the top wall 31 terminates in a rounded front edge 32, and the front portion of the top wall extends forwardly substantially beyond the wing portions 25 and 26 of the head portion.

Referring to FIGS. 1 and 4, a slot 33 is provided in the right curved shoulder portion 29. An elastic strap 19a is attached to the outside surface of the shoulder portion by a pair of rivets 34 and extends through the slot 33. A similar slot 35 is provided in the left shoulder portion for the strap 20a which is also attached to the outside surface of the brace by rivets. Conventional buckles 36 are attached to the ends of the straps 19a and 20a.

A pair of elastic straps 20b and 21a (FIG. 1) are attached to the rear surface of the bottom of the brace at the right side thereof, and a pair of elastic straps 19b and 21b are attached at the left side. A buckle 36 is attached to the strap 21a. If desired, the two pairs of straps 21a and 21b and 19b and 20b can be formed from two straps which extend across the rear surface of the brace from one side to the other.

The straps 19a and 19b and 20a and 20b may be connected by the buckles 36 to form the crossing straps 19 and 20 shown in FIG. 2. The straps 21a and 21b may be connected to form the chest strap 21.

Traction is applied to the patient in FIG. 2 by a Sayre head halter 38 and a pair of elastic straps 39 and 40. The Sayre halter is well known and need not be described in detail. The halter includes a chin strap 41a which extends under the patient's chin and an occiput strap 41b (FIG. 1) which extends behind the head. The ends of the chin strap and occiput strap on each side of the halter are attached to the ends of straps 42 and 43 which are looped through attaching rings 44 and 45, respectively (see also FIG. 6). When the chin strap and occiput strap are positioned about the patient's head, the straps can be prevented from separating by connecting straps 41c (FIGS. 1 and 3) which are connected to the occiput strap and which can be releasably connected to the chin strap by, for example, Velcro fasteners.

The top wall 31 of the brace is provided with a pair of slots 46 and 47 adjacent the V-shaped walls 23 and 24 of the head portion of the brace (FIG. 4). The elastic straps 39 and 40 extend through the slots 46 and 47, respectively, and are looped through the attaching rings 44 and 45 of the halter.

Referring to FIGS. 5 and 6, one end 48 of the strap 39 is attached to the outside surface of the wall 23 by a rivet 49, and the other end 50 of the strap passes through a clip 51 which is secured to the wall 23 by a strap 52 and rivet 53. The looped intermediate portion 54 of the strap 39 extends through the slot 46 in the top wall and around the ring 44. The other elastic strap 40 is similarly attached to the wall 24.

The clip 51 is illustrated in FIG. 7 and is of the type which comprises a base portion 55, which is provided with a pair of slotted openings 56 and 57 for the straps 39 and 52, and a keeper 58, which is pivotally mounted on the base portion. The keeper has a serrated edge 59 which is engageable with the strap 39, and the keeper is spring-biased against the strap. The serrations prevent the strap from being pulled through the clip in the direction of the arrow A, but the strap may be pulled freely in the direction of the arrow B. Pressure on the strap may be released by pushing on the thumb portion 60 of the keeper to pivot the keeper and to permit the strap to be pulled in the direction of the arrow A.

The wing portions 25 and 26 of the head portion of the orthosis are provided with elongated slots 62 and 63 (FIG. 1) for the forehead strap 22. A cushion pad 64 is attached to the middle of the strap, and a fastening strip of the type which is sold under the name Velcro is attached to the strap opposite the pad. After the pad is positioned on the forehead of the patient, the ends of the strap are passed through the slots 62 and 63 and pulled back and secured to the fastening strip.

The orthosis is applied to the patient by positioning the shoulder portion 16 behind the shoulders of the patient so that his shoulders engage the curved portions 29 and 30 and his head lies in the cushioned V-shaped head section. The three pairs of chest straps 19a–19b, 20a–20b, and 21a–21b are then joined and pulled tightly about the chest. The buckles 36 can be similar to the clip 51 described with respect to FIG. 7 so that the straps can be tightened merely by pulling the free end of the straps through the buckles. The Sayre head halter, which is already attached to the elastic straps 39 and 40, is then positioned about the head, and the halter is tensioned by pulling the free ends of the straps 39 and 40 which extend through the clips 51.

Referring again to FIG. 6, the looped strap 39 provides a pulley action on the ring 44 when the free end 50 of the strap is pulled. The looped end of the strap slides freely through the metal ring 44, and the tension on the strap 42 of the halter can therefore be adjusted gradually and smoothly. The looped portion of the strap forms two layers at the edge of the slot 46 through the top wall 31, and the layer which engages the edge of the slot does not move when the free end of the strap is pulled. This layer protects the layer which does move from being abraded by the edge and minimizes the friction on the moving layer.

After both of the straps 39 and 40 have been tensioned to provide the desired traction, the forehead strap 21 can be fastened over the forehead of the patient. The elongated slots 62 and 63 permit the forehead strap to be properly aligned with the forehead.

The head, neck, and thoracic spine of the patient are now immobilized, and the patient can be transported without changing the relationship between the head, neck, and thoracic spine and without fear of further injury to the cervical spine. Either traction or stability of the head and neck can be provided by the elastic straps 39 and 40 without the use of weights, and the tension in the elastic straps 39 and 40 will be constant throughout transport regardless of the movements of the vehicle.

FIG. 3 illustrates the manner in which the patient can be rolled to a lateral position during emesis merely by rolling the patient in the normal manner. This can be accomplished by a single attendant, and the head, neck, and thoracic spine relationship will remain constant. The laterally extending wing portions 25 and 26 of the head portion may be made sufficiently wide so that one of the wings engages the supporting surface when the patient is rolled to a lateral position in order to support the orthosis and to maintain the longitudinal axis of the orthosis generally horizontal. The patient can also be resuscitated while in the orthosis without changing the relationship between the head, neck, and thoracic spine.

The orthosis can also be used when traction is being applied by skeletal tongs. FIG. 8 illustrates a patient to whom Gardner-Wells skeletal tongs 66 have been applied. The crescent-shaped tongs are attached to the skull by pins 67 and 68, and a cord or rope 69 is attached to the top of the tongs by an S-hook or the like. The cord extends through an elongated slot 70 in the top wall (see also FIGS. 1 and 4), and the free end of the cord is anchored by a cleat 71 (FIGS. 3, 5, 9, and 10) on the upper surface of the top wall. The cleat includes a base 72 (FIG. 9) which is attached to the top wall by rivets 73 and a pair of spaced walls 74 and 75 which form a wedge-shaped groove or recess 76. The confronting surfaces of the walls are provided with a plurality of parallel ridges 77 which extend at an obtuse angle with respect to a line from the cleat to the slot 70. The cord is pulled to provide the desired traction and then anchored by pulling it downwardly into the wedge-shaped groove of the cleat. The ridges provide a sufficient frictional retention force on the cord to maintain the traction.

When tongs are used, the head halter is unnecessary and may be removed by withdrawing the free ends of the straps 39 and 40 through the clips 61 and the attaching rings 44 and 45 of the halter. If desired, however, the straps 39 and 40 can be attached to the tongs to apply the traction force on the tongs rather than the cord 69.

While in the foregoing specification a detailed description of a specific embodiment of the invention was set forth for the purpose of illustration, it is to be understood that many of the details herein given may be varied considerably by those skilled in the art without departing from the spirit and scope of the invention.

I claim:

1. A device for immobilizing the cervical spine and cranium of a patient comprising an orthosis having a shoulder portion adapted to conform generally to the back of the shoulders of a patient, a generally V-shaped head portion having a lower end joined to the shoulder portion and an upper end, and a top portion extending across the upper end of the V-shaped head portion, a strap attached to the shoulder portion for strapping the orthosis to a patient so that the shoulder portion engages the shoulders of the patient and the inside of the V-shaped head portion engages the head of the patient and the top portion is spaced above the head of the patient, a pair of clips mounted on the outside of the V-shaped head portion on opposite sides thereof, a pair of elastic straps, each of the elastic straps having a first end portion secured to the outside of the V-shaped head portion, a looped intermediate portion extending through an opening in the top portion, and a second end portion extending through one of the clips, and a halter adapted to engage the head of the patient, the halter including a ring for each of the elastic straps through which the looped intermediate portion of the strap extends whereby tension on the elastic straps and the halter can be adjusted by pulling the second end portions of the straps through the clips.

2. The device of claim 1 including a cushion attached to the inside of the V-shaped head portion.

3. The device of claim 1 in which the head portion includes a pair of side portions which extend laterally outwardly from the upper ends of the V-shaped portion, and a strap extending between the two side portions of the head portion.

4. The device of claim 1 in which the shoulder portion includes a substantially flat portion adapted to engage the back of the patient and a curved portion adjacent the head portion adapted to engage the upper part of the shoulders of the patient.

5. A device for immobilizing the cranium and cervical spine of a patient comprising an orthosis having a shoulder portion, a V-shaped head portion, and a top portion extending transversely across the V-shaped head portion, means for attaching the orthosis to a patient so that the shoulder portion engages the shoulders of the patient and the V-shaped head portion engages the head of the patient with the top portion extending over the head, a halter adapted to engage the head of the patient, a pair of elastic straps connected to the halter and extending through the top portion of the orthosis, and means for adjustably securing each of the elastic straps to the orthosis whereby the elastic straps and the halter can be tensioned to apply traction to the patient.

6. A device for immobilizing the cranium and cervical spine of a patient comprising an orthosis having a shoulder portion, a head portion, and a top portion, the head portion being generally V-shaped in transverse cross section and including a pair of side portions which extend laterally outwardly from the upper ends of the V-shaped portion, the top portion extending transversely across the V-shaped head portion, means for attaching the orthosis to a patient so that the shoulder portion engages the shoulders of the patient and the head portion engages the head of the patient with the top portion extending over the head, stabilizing means attached to the orthosis and extending from the top portion for immobilizing the cranium and cervical spine of the patient and for applying traction to the cervical spine, and a strap extending between the two transversely outwardly extending side portions of the head portion for engaging the head of the patient.

7. The device of claim 6 including a cushion attached to the inside of the V-shaped head portion.

8. The device of claim 6 in which the shoulder portion includes a substantially flat portion adapted to engage the back of the patient and a curved portion adjacent the head portion adapted to engage the upper part of the shoulders of the patient.

9. A device for immobilizing the cranium and cervical spine of a patient comprising an orthosis having a shoulder portion, a head portion, and top portion, means for attaching the orthosis to a patient so that the shoulder portion engages the shoulders of the patient and the head portion engages the head of the patient with the top portion extending over the head, and stabilizing means attached to the orthosis and extending from the top portion for immobilizing the cranium and cervical spine of the patient and for applying traction to the cervical spine, the stabilizing means including a halter and a pair of elastic straps, each of the elastic straps having a first end portion secured to the orthosis, a looped intermediate portion extending through an opening in the top portion of the orthosis, and a second end portion extending through a clip mounted on the orthosis, the halter including a ring for each of the elastic straps through which the looped central portion of the strap extends whereby tension on the elastic straps and the halter can be adjusted by pulling the second end portions of the straps through the clips.

* * * * *